United States Patent [19]

Mason

[11] Patent Number: 5,062,437
[45] Date of Patent: Nov. 5, 1991

[54] DENTAL FLOSSING TOOL

[76] Inventor: Robert F. Mason, 10763 Hedda Pl., Cerritos, Calif. 90701

[21] Appl. No.: 502,800

[22] Filed: Apr. 2, 1990

[51] Int. Cl.⁵ .............................................. A61C 15/00
[52] U.S. Cl. .................................................... 132/323
[58] Field of Search ............... 132/323, 324, 325, 326, 132/327

[56] References Cited

U.S. PATENT DOCUMENTS

| | | | |
|---|---|---|---|
| 2,109,417 | 2/1938 | Elcan | 132/325 |
| 3,901,251 | 8/1975 | Johnston | 132/326 |
| 4,050,470 | 9/1977 | Miller | 132/323 |
| 4,403,625 | 9/1983 | Sanders et al. | 132/323 |
| 4,638,824 | 1/1987 | De La Hoz | 132/323 |
| 4,926,820 | 5/1990 | Wearn | 132/323 |

Primary Examiner—Gene Mancene
Assistant Examiner—Michael Lynch
Attorney, Agent, or Firm—Robert M Sperry

[57] ABSTRACT

A cap for frictional retention on an existing dental flossing tool to enhance protection of the dental flossing material when the tool is not in use and which can be removed, when desired, and which includes means for retaining one end of a strand of dental flossing material to enable the cap to function as an auxiliary handle for cooperation with the dental flossing tool to permit the flossing operation to be performed without having the user's hands contacting the flossing material.

9 Claims, 1 Drawing Sheet

DENTAL FLOSSING TOOL

BACKGROUND

1. Field of Invention

This invention relates to dental flossing tools and is particularly directed to a tool for releasably retaining one end of a strand of dental flossing material to facilitate manipulating the floss between the user's teeth.

2. Prior Art

As is well known, the use of dental flossing material is an important part of proper dental hygiene. Unfortunately, many people do not make a regular habit of flossing their teeth. One reason for this is that dental flossing material is conventionally sold in open spools and that it is necessary to manually unreel a desired quantity of flossing material and to hold the flossing material between one's fingers to perform the flossing operation, while attempting to manipulate the flossing material through the spaces between adjacent teeth. This manipulation requires some effort and it is often difficult to get an adequate grip on the strand of flossing material to enable such manipulation. Thus, the user's fingers frequently slip off of the strand of flossing material and the strand may brush against an unsanitary surface and, hence, be wasted. To avoid this problem, many users wrap several coils of the flossing material about their forefinger to prevent slippage. Unfortunately, this necessitates considerable waste of the flossing material. Moreover, such wrapping may become painful, as the flossing material is worked between the teeth and also may cut off blood circulation to the finger tip. To overcome these objections, numerous types of dental flossing tools have been proposed. Unfortunately, most of the prior art dental flossing tools have been relatively bulky, complex and expensive. Thus, none of the prior art dental flossing tools have been entirely satisfactory.

BRIEF SUMMARY AND OBJECTS OF INVENTION

These disadvantages of prior art dental flossing tools are overcome with the present invention and means is provided which is simple, compact and inexpensive.

The advantages of the present invention are preferably attained by providing a dental flossing tool which includes means for frictionally retaining one end of a strand of dental flossing material mounted on a suitable handle to securely, yet releasably, retain one end of a strand of dental flossing material while the other hand manipulates the strand of flossing material between the user's teeth, thus giving the user the option of using either their thumb, forefinger or index finger for guiding the flossing material between adjacent teeth. If desired, the flossing tool of the present invention may be formed with a hollow handle which can serve as a cap for conventional dental flossing tools to protect the tip of such tools and any exposed flossing material from contamination during storage and to releasably retain one end of the dental flossing material during flossing operations.

Accordingly, it is an object of the present invention to provide improved means for performing dental flossing operations.

Another object of the present invention is to provide improved means for performing dental flossing operations which permit the flossing operation to be securely retained without requiring the user to wrap the flossing material about a finger.

A further object of the present invention is to provide improved means for performing dental flossing operations which can be used with existing dental flossing tools to permit the flossing operation to be performed while permitting the user the option of using either their thumb, forefinger or index finger to guide the flossing material between adjacent teeth.

An additional object of the present invention is to provide improved means for performing dental flossing operations which serves to enhance protection of the flossing material in existing dental flossing tools, when the tool is not in use, and which cooperates with the tool to permit the flossing operation to be performed without the user's hands contacting the flossing material.

A specific object of the present invention is to provide improved means for performing dental flossing operations comprising means for frictionally retaining one end of a strand of dental flossing material mounted on a suitable handle to securely, yet releasably, retain one end of a strand of dental flossing material while the other hand manipulates the strand of flossing material between the user's teeth, thus giving the user the option of using either their thumb, forefinger or index finger for guiding the flossing material between adjacent teeth. If desired, the flossing tool of the present invention may be formed with a hollow handle which can serve as a cap for conventional dental flossing tools to protect the tip of such tools and any exposed flossing material from contamination during storage and to releasably retain on end of the dental flossing material during flossing operations.

These and other objects and features of the present invention will be apparent from the following detailed description, taken with reference to the figures of the accompanying drawing.

DETAILED DESCRIPTION OF THE INVENTION

Figure 1:
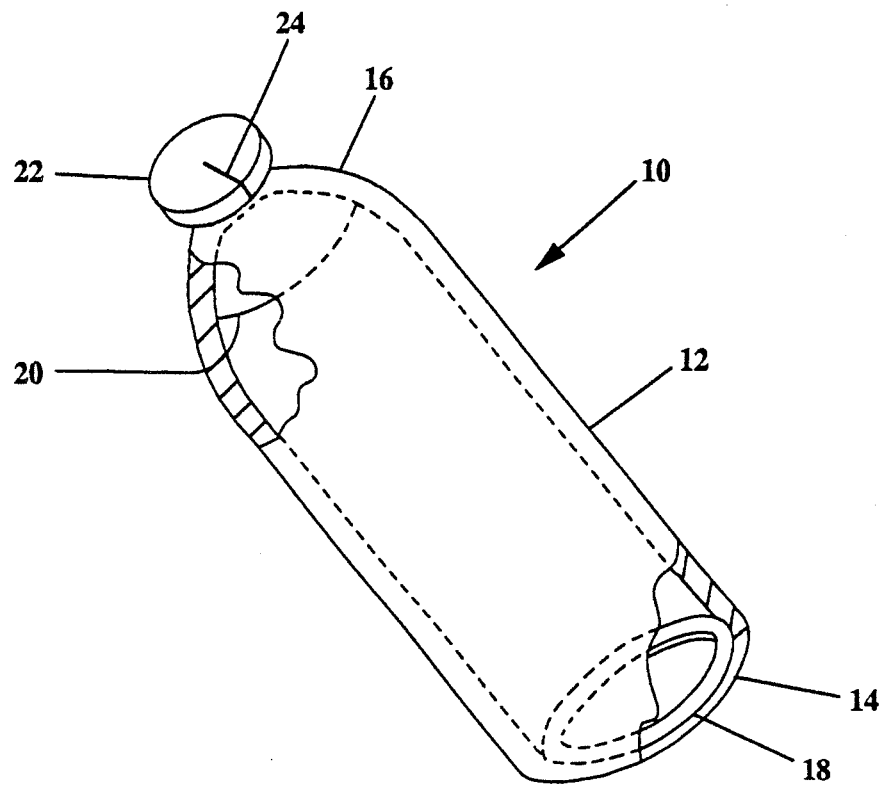
FIG. 1 is an isometric view, with portions broken away for clarity, showing a device embodying the present invention.

In that form of the present invention chosen for purposes of illustration, FIG. 1 shows a dental flossing tool, indicated generally at 10, comprising an elongated, generally cylindrical member 12 having an open end 14 and a closed end 16. The length of the cylindrical member 12 is preferably such that it can conveniently be held in the user's hand, while the diameter of the cylindrical member 12 is such that it can surround the tip, not shown, of a conventional dental flossing tool and will provide a releasable, friction fit with the dental flossing tool. If desired, suitable means, such as O-ring 18 may be provided adjacent the open end 14 of the cylindrical member 12 to provide a moisture-proof seal with the tip of the dental flossing tool to protect that portion of the flossing material which normally projects from the tip of the dental flossing tool. Furthermore, if desired, a pad 20 of suitable material may be mounted within the cylindrical member 12 adjacent the closed end 16 which may serve as a moisture absorbent or may contain a suitable disinfectant or antiseptic substance to provide further protection for the flossing material. On the outside of the closed end 16 of the cylindrical member 12 is mounted a disc 22 having a slot 24 formed therein and sized to frictionally retain a strand of flossing material inserted into the slot 24.

In use, the tool 10 may be placed over the tip of a dental flossing tool for storage and will frictionally engage the tip of the dental flossing tool to retain itself on the tool. At the same time, the friction grip of the cap 10, or O-ring 18, if provided, will form a moisture-proof seal with the tool to prevent moisture from reaching and contaminating the tip of the tool and that portion of the flossing material which normally projects from the tip of the dental flossing tool. Moreover, if provided, the pad 20 will provide additional moisture absorption and may dispense a suitable disinfectant or antiseptic substance to provide further protection for the flossing material. When the user desired to perform the flossing operation, they remove the cap 10 from the tip of the dental flossing tool and place a portion of the strand of flossing material in the slot 24 of the disc 22. As noted above, the slot 24 is sized to frictionally retain the strand of flossing material. Moreover, if desired, the flossing material may be wound about the closed end 16 of the cap 10 to assure more positive retention of the strand of flossing material. The user may then hold the dental flossing tool in one hand and hold the cap 10 in the other hand, as an auxiliary flossing tool, and may proceed to perform the flossing operation. The tip of the dental flossing tool may be inserted into the user's mouth to guide one end of the strand of flossing material in movement between the user's teeth, while the cap 10 retains the end of the strand flossing material which is outside the user's mouth. When the flossing operation has been completed, the used portion of the strand of flossing material may be severed and discarded, in the usual manner, and the cap 10 may again be placed on the tip of the dental flossing tool for storage and to serve as a protective cap.

Alternatively, if desired, the tool 10 may be used manually by engaging one end of a strand of dental flossing material in the slit 24 to frictionally retain that end of the strand of flossing material. The user may then sever a desired length of the flossing material and may grip the free end of the flossing material in their fingers to perform the flossing operation. When this is done, the tool 10 may be held by gripping the handle 12 between the palm of the hand and the last three fingers of that hand, which enables the user to have the option of using either their thumb, forefinger or index finger for guiding the flossing material between adjacent teeth.

Figure 2:
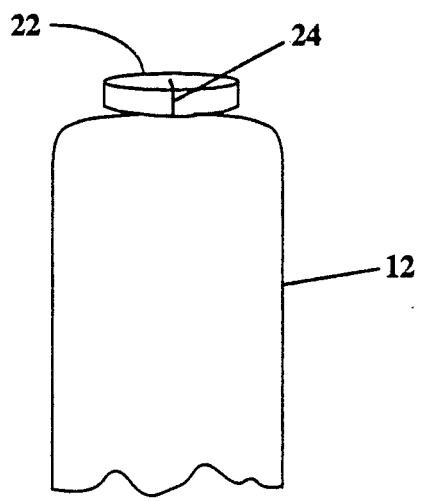
FIG. 2 is a side view of an alternative form of the device of FIG. 1.

FIG. 2 shows a side view of an alternative form of the dental flossing tool of FIG. 1. In this form of the present invention, the handle 12 is formed solid to provide a stronger handle for gripping by the user's hand. This form of the tool 10 is used manually, in the same manner as described above for the device of FIG. 1.

Obviously, numerous variations and modifications can be made without departing from the spirit of the present invention. Therefore, it should be clearly understood that the forms of the present invention described above and shown in the figures of the accompanying drawing are illustrative only and are not intended to limit the scope of the present invention.

What is claimed is:

1. An auxiliary dental flossing tool comprising:
   an elongated, generally cylindrical handle member (formed for insertion into a user's mouth to facilitate manipulation of one end of a strand of flossing material during a flossing operation), and
   a generally button-shaped disc fixedly mounted on the outside of said handle and forming a floss retaining V-shaped recess between and at the base of said disc and said handle member for releasable frictional retention of a strand of flossing material, (having at least one slot formed therein to frictionally retain a strand of flossing material mounted on the outside of said handle and forming a floss retaining recess between said disc and said handle member for releasable frictional retention of a strand of flossing material) and
   at least one non-expandable slot extending part way through said disc to frictionally lock the end of a strand of dental floss within said slot from unwinding.
2. The device of claim 1 wherein:
   said cylindrical member has a length such that it may conveniently be held in a user's hand.
3. The device of claim 1 further comprising:
   said cylindrical member being hollow and having an open end and a closed end and having said disc mounted adjacent said closed end and forming said floss retaining recess between said disc and said closed end of said cylindrical member.
4. The device of claim 3 wherein:
   said cylindrical member is sized to surround and frictionally engage the tip of a dental flossing tool.
5. The device of claim 4 further comprising:
   sealing means mounted adjacent said open end of said cylindrical member and engageable with the tip of said dental flossing tool when said device is positioned thereon to provide a moisture-proof seal between said device and said dental flossing tool.
6. The device of claim 3 further comprising:
   a pad of moisture absorbent material mounted within said closed end of said cylindrical member.
7. The device of claim 3 further comprising:
   a pad of material mounted within said closed end of said cylindrical member containing a quantity of an antiseptic material.
8. The device of claim 3 further comprising:
   a pad of material mounted within said closed end of said cylindrical member containing a quantity of a disinfectant material.
9. The device of claim 1 wherein:
   said slot is dimensioned to frictionally retain said strand of flossing material.

* * * * *